United States Patent [19]

Glimcher et al.

[11] Patent Number: 5,691,397
[45] Date of Patent: *Nov. 25, 1997

[54] ISOLATION OF THE CALCIUM-PHOSPHATE CRYSTALS OF BONE

[75] Inventors: Melvin J. Glimcher, Boston, Mass.; Hyun-Man Kim, Seoul, Rep. of Korea; Christian Rey, Castanet, France

[73] Assignee: Children's Medical Center Corporation, Boston, Mass.

[*] Notice: The term of this patent shall not extend beyond the expiration date of Pat. No. 5,565,502.

[21] Appl. No.: 728,820

[22] Filed: Oct. 10, 1996

Related U.S. Application Data

[63] Continuation of Ser. No. 409,755, filed as PCT/US94/03214, Mar. 24, 1994, Pat. No. 5,565,502, which is a continuation-in-part of Ser. No. 36,412, Mar. 24, 1993, Pat. No. 5,439,951.

[51] Int. Cl.$^6$ .............................. C08K 3/32; C08K 3/36; A61F 2/02; A61F 2/28
[52] U.S. Cl. .......................... 523/115; 424/423; 424/426; 623/16; 264/344
[58] Field of Search .............................. 523/115; 424/423, 424/426; 623/16; 264/344

[56] References Cited

U.S. PATENT DOCUMENTS

| 5,167,961 | 12/1992 | Lussi et al. | 424/423 |
| 5,425,769 | 6/1995 | Snyders, Jr. | 623/16 |

FOREIGN PATENT DOCUMENTS

| 2097409 | 4/1990 | Japan . |
| 3109210 | 5/1991 | Japan . |
| 92-288770 | 8/1992 | Japan . |
| 4198007 | 12/1992 | Japan . |

OTHER PUBLICATIONS

Aberman, H. M., et al., "Gap healing in a non-weight bearing dog model: effectiveness of a solution precipitated apatite coating," *Thirty Ninth Annual Meeting, Orthopaedic Research Society* 18:466 (1993).

Aspenberg, P., et al., "Bone morphogenetic protein induces bone in the squirrel monkey, but bone matrix does not," *Thirty Ninth Annual Meeting, Orthopaedic Research Society* 18:101 (1993).

Atkin, et al., "Enhancement of Osteoinduction by Vitamin D Metabolites in Rachitic Host Rats," *J. Bone Miner. Res.* 7(8):863–875 (1992).

Ballock, R.T., et al., "Regulation of collagen expression in periosteal cells by three members of the TGF-B superfamily," *Thirty Ninth Annual Meeting, Orthopaedic Research Society* 18:734 (1993).

Bauer, et al., "Hydroxyapatite–Coated Femoral Stems, Histological Analysis of Components Retrieved at Autopsy," *J. Bone Joint, Surg.* 10:1439–1452 (1991).

Bioebaum, et al., "Retrieval Analysis of a Hydroxyapatite–Coated Hip Prosthesis," *Clin. Orthop,* 267:97–102 (1991).

Bonar, et al., "Structural and composition studies on the mineral of newly formed dental enamel; a chemical, x–ray diffraction, and $^{31}$P and proton nuclear magnetic resonance study," *J. Bone Min. Res.* 6:1167–1176 (1991).

Bragdon, C.R., et al., "The histology of bone ingrowth at the implant/bone interface under known amounts of micromotion" *Thirty Ninth Annual Meeting, Orthopaedic Research Society* 18:468 (1993).

(List continued on next page.)

Primary Examiner—Carlos A. Azpuru
Attorney, Agent, or Firm—Arnall Golden & Gregory, LLP

[57] ABSTRACT

The present invention is a process for first removing and isolating the calcium-phosphate crystals of bone from a substantial amount of the organic matrix and cellular constituents of bone without significant physical, chemical or structural alterations in the crystals. The crystals can then be further treated to remove the remaining amount of organic material associated with the crystals, leaving them essentially free of any of the organic constituents of bone, without significant physical, chemical or structural alterations in the crystals.

17 Claims, 1 Drawing Sheet

OTHER PUBLICATIONS

Burke, D.W., et al, "Mechanical aspects of the bone–porous surface interface under known amounts of implant motion; an in vivo canine study," *Thirty Ninth Annual Meeting, Orthopaedic Research Society* 18:470 (1993).

Cesniai, et al., "Decreased Osteoinductive Potential of Bone Matrix From Ovarlectomized Rats," *Acta Orthop, Scand,* 62(5):471–475 (1991).

Cohen–Solal, et al., "Identification of organic phosphorus covalently bound to collagen and non–collagenous proteins of chicken–bone matrix: the presence of O–phosphoserine and O–phosphothreonine in non–collagenous proteins, and their absence from phosphorylated collagen" *Biochem. J.* 177:81–98 (1979).

Cook, "Hydroxyapatite–Coated Total Hip Replacement," *Dent. Clin. North Am.* 36:235–238 (1992).

Cook, et al., "Early Clinical Results with the Hydroxyapatite–Coated Porous LSF Total Hip Systems," *Dent. Clin. North Am.* 36(1):247–255 (1992).

Cook, S.D., et al., "Recombinant human osteogenic protein–1 (rhOP–1) heals segmental long–bone defects in non–human primates,"0 *Thirty Ninth Annual Meeting, Orthopaedic Research Society* 18:484 (1993).

Cook, S.D., et al. "Restoration of large diaphyseal segmental defects in rabbits using recombinant human osteogenic protein (OP–1)," *Combined meetings of Orthopaedic Research societies of USA, Japan and Canada* 1:65 (1991).

Cordoba, et al., "Effect of microcrystalline hydroxyapatite on bone marrow stromal cell osteogenesis", *Thirty Ninth Annual Meeting, Orthopaedic Research Scoiety* 102 (1993).

Costantino, et al., "Hydroxyapatite Cement," *Arch. Otolaryngol, Head Neck Surg.* 117(4):379–384 (Apr. 1991).

Costantino, et al., "*Experimental Hydroxyapatite Cement Cranioplasty,*" *Plast. Reconstr. Surg.* 90(2):174–185 (1992).

Csongradi, and Maloney, "Ununited Lower Limb Fractures," *West J. Med.* 150(6):675–680 (1989).

D'Antonio, et al., "Hydroxylapatite–Coated Hip Implants, Multicenter Three–Year Clinical and Roentgenographic Results," *Clin. Orthop.* 285:102–115 (1992).

D'Antonio, et al., "Early Clinical Experience with Hydroxyapatite–Coated Femoral Implants," *J. Bone Joint Surg.* 74(7):995–1008 (1992).

de Bruin, et al., "Structural arrangements at the interface between plasma sprayed calcium phosphates and bone," *Biomaterials* 15:543–550 (1994).

Dorr and Smith, "Clinical Results from the Calcitite–Coated Press Fit APR Hip System," *Dent. Clin. North Am.* 36:239–246 (1992).

Drucker, et al., "Works in Progress #6, Total Hip Arthroplasty Using a Hydroxyapatite–Coated Acetabular and Femoral Component," *Orthop. Rev.* 20:179–185 (1992).

Frayssinet, et al., "New Observations on Middle Term Hydroxyapatite–Coated Titanium Alloy Hip Prostheses," *Biomaterials* 13(10):668–674 (1992).

Freeman, "Hydroxyapatite Coating of Prostheses," *J. Bone Joint Surg. Br.* 74(6):933–934 (1992).

Friedman, et al., "Hydroxyapatite Cement," *Arch Otolaryngol, Head Neck Surg.* 117(4):385–389 (Apr. 1991).

Furlong and Osborn, "Fixation of Hip Prostheses by Hydroxyapatite Ceramic Coatings," *J. Bone Joint Surg.* 73:741–745 (1991).

Gatti and Zaffe, "Short–term Behaviour of Two Similar Active Glasses Used as Granules in the Repair of Bone Defects," *Biomaterials* 12(5):497–504 (1991).

Glimcher, M.J., "A basic architectural principle in the organization of mineralized tissues" *Clin. Orthop.* 61:16–36 (1968).

Glimcher M.J., "Molecular biology of mineralized tissues with particular reference to bone," *Rev. Mod. Physics* 31:3590–393 (1959).

Glimcher, et al., "Recent Studies of Bone Mineral: Is the Amorphous Calcium Phosphate Theory Valid?" *J. of Crystal Growth* 53:100–119 (1981).

Glowacki, et al., "Demineralized Bone Implants," *Clin. Plast. Surg.* 12(2):233–241 (1985).

Glowacki, J., et al., "The role for osteocalcin in osteoclast differentiation" *J. Cellular Biochem* 45:292–302 (1991).

Goldberg and Stevenson, "Natural history of autografts and allografts," *Clin. Orthop,* 225:7–16 (1987).

Groessner–Schreiber, et al., "Bone Cell Response to Hydroxyapatite–Coated Titanium Surfaces In Vitro," *Seminars in Arthroplasty* 2:260–267 (1991).

Greis, et al., "A Long–Term Study on Defect Filling and Bone Ingrowth Using a Canine Fiber Metal Total Hip Model," *Clin. Orthop.* 274:47–59 (1992).

Gutkin, et al., "Alkaline and Acid Phosphatase Activity in the Dynamics of Ectopic Osteogenesis," *Stomatologiia (Mosk)* (2):18–20 (1992).

Harada, "Hydroxyapatite Tricalcium Phosphate (TCP)–" Experimental Studies of Healing on Compound Blocks of Hydroxyapatite (HAP) Particles and Tricalcium Phosphate (TCP) Powder Implantation in Rabbit Mandible–Comparison of HAP/TCP ratios and plastic methods, Department of Oral and Maxilloacial Surgery, Tokyo Dental College, *Shikwa–Gakuho* 89(2):263–297 (1989).

Hardy, et al., "Bonding of Hydroxyapatite–Coated Femoral Prostheses, Histopathology of Specimens from Four Cases," *J. Bone Joint Surg.* 73:732–740 (1991).

Hollis, M.J., et al., "Effect of micromotion on ingrowth into porous coated implants," *Thirty Ninth Annual Meeting, Orthopaedic Research Society* 18:472 (1993).

Hunt, T.R., et al., "Healing of a segmental defect in the rat femur using a bone inducing agent (BIA) derived from a cultured human osteosarcoma cell line (SAOS–2)," *Thirty Ninth Annual Meeting, Orthopaedic Research Society* 18:489 (1993).

Iwasaki, M., et al., "Bone morphogenetic protein–2 stimulates osteogenesis in high density culture of periosteum–derived cells," *Thirty Ninth Annual Meeting, Orthopaedic Research Society* 18:483 (1993).

Jergesen, et al., "Age Effects on Bone Induction by Demineralized Bone Powder," *Clin. Orthop.* 268:253–259 (1991).

Katthagen, "Bone Induction with Bone Morphogenic Protein." *Z–Orthop.* 125(5):559–566 (1987).

Kim, et al., "Isolation of Calcium–Phosphate Crystals of Mature Bovine Bone by reaction with Hydrazine at Low Temperature," *Hydroxyapatite and Related Materials* pp. 331–337 (Brown and Constantz, Editors, CRC Press, 1994).

Kim, et al., "Isolation of Calcium–Phosphate Crystals by Non–Aqueous Methods at Low Temperature," *J. of Bone and Mineral Res.* 10:1589–1601 (1995).

Kroon and Freeman, "Hydroxyapatite Coating of Hip Prostheses, Effect on Migration into the Femur," *J. Bone Joint Surg.* 74(4):518–522 (1992).

Kubler and Urist, "Allogenic Bone and Cartilage Morphogenesis. Rat BMP in Vivo and in Vitro," *J. Craniomaxillofac. Surg.* 19(7):283–288 (1991).

Landis, et al., "Electron microscopic observations of bone tissue prepared anhydrously in organic solvents." *J. Ultrastruct. Res.* 59:1–30 (1977).

Landis, et al., "Electron microscopic observations of bone tissues prepared by ultracryomicrotomy" *J. Ultrastruct. Res.* 59:185–206 (1977).

Landis, et al., "Electron diffraction and electron probe microanalysis of the mineral phase of bone tissue prepared by anhydrous techniques," *J. Ultrastruct. Res.* 63:188–223 (1978).

Lee and Glimcher, "Three–dimensional spatial relationship between the collagen fibrils and the inorganic calcium phosphate crystals of pickerel (*Americanus americanus*) and herring (*Clupea harengus*) bone," *J. Mol. Biol.* 217:487–501 (1991).

Maistrelli, et al., "Hydroxyapatite Coating on Carbon Composite Hip Implants in Dogs," *J. Bone Joint Surg.* 74(3):452–456 (1992).

Manley and Koch, "Clinical Results with the Hydroxyapatite–Coated Omnifit Hip Stem," *Dent. Clin. North Am.* 36(1):257–262 (1992).

Marchandise, et al., "Solid–State $^{31}$P NMR Spectroscopy ofBone and Bone Substitutes," *Magn. Reson. Med.* 28(1):1–8 (1992).

Marden, et al., "Growth and Differentiation Factors: Role in Bone Induction and Potential Application in Craniofacial Surgery," *J. Craniofac. Surg.* 1(3):154–160 (Jul. 1990).

Miyamoto, S., et al., "Trans–filter bone induction in monkeys by bone morphogenetic protein" *Thirty Ninth Annual Meeting, Orthopaedic Research Society* 18:99 (1993).

Monglorgi, et al., "Influence of Calcitonin Treatment on the Bone Structure and Mineral Content in Osteoarthritis," *Boll. Soc. Ital. Biol. Sper.* 68(2):85–89 (1992).

Ohgushi, et al., "Repair of bone defects with marrow cells and porous ceramic," *Acta Orthop. Scand.* 60(3):334–339 (1989).

Ono, et al., "Quantitative study on osteoconduction of apatite–wollastonite containing glass ceramice granules, hydroxyapatite granules, and alumina granules," *Biomaterials* 11(4):265–271 (May 1990).

Oonishi, "Orthopaedic Applications of Hydroxyapatite," *Biomaterials* 12:171–178 (1991).

Parrish, et al., "The Effect of Hyperthermia on the Incorporation of Cortical Bone Autografts: A Histomorphometric and Biomechanical Study," *41st Annual Meeting, Orthopaedic Research Society* 81–14 (1995).

Passuti, et al., "Macroporous Calcium Phosphate Ceramic Performance in Human Spine Fusion," *Clin. Orthop.* 248:169–176 (Nov. 1989).

Passuti, et al., "Calcium Phosphate Ceramics in Orthopedic Surgery," *Presse–Med.* 18(1):28–31 (1989).

Pinholt, et al., "Alveolar Ridge Augmentation by Osteoinductive Materials in Goats," *Scand. J. Dent. Res.* 100(6):361–365 (1992).

Pinholt, et al., "Bone Induction by Composites of Bioresorbable Carriers and Demineralized Bone in Rats: A Comparative Study of Fibrin–Collagen Paste, Fibrin Sealant, and Polyorthoester with Gentamicin," *J. Oral Maxillofac. Surg.* 50(12):1300–1304 (1992).

Pinholt, et al., "Chemical, Physical, and Histologic Studies on Four Commercial Apatites Used for Alveolar Ridge Augmentation," *J. Oral Maxillofac. Surg.* 50(8):859–867 (Aug. 1992).

Pinholt, et al., "Alveolar ridge augmentation in rats by Bio–Oss," *Scan. J. Dent. Res.* 99(2):154–161 (Apr. 1991).

Pochon, et al., "Knochenersatzplastiken mit Beta–Tricalciumphosphat–Resultate experimenteller Studien und erste klinische Fallbiespiele," *Z–Kinderchir.* 41(3):171–173 (1986).

Prolo and Oklund, "Composite Autogeneic Human Cranioplasty: Frozen Skull Supplemented with Fresh Lilal Corticocancellous Bone," *Neurosurgery* 15(6):846–851 (1984).

Rao, et al.,"Posterior Cervical Spine Stabilization under Local Anesthesia," *J. Spinal, Disord.* 3(3):250–254 (1990).

Rey, et al., "Resolution–Enhanced Fourier Transform Infrared Scpectroscopy Study of the Environment of Phosphate Ion in the Early Deposits of a Solid Phase of Calcium Phosphate in Bone and Enamel and their Evolution with Age: 2. Investigations in the $v_3$ PO$_4$ Domain," *Calcif. Tissue Int.* 49:383–388 (1991).

Rey, et al., "Resolution–Enhanced Fourier Transform Infrared Spectroscopy Study of the Environment of Phosphate Ions in the Early Deposits of a Solide Phase of Calcium–Phosphate in Bone' and Enamel, and their Evolution with Age. I: Investigations in the $v_4$ PO$_4$ Domain," *Calcif. Tissue Int.* 46:384–394 (1990).

Rey, et al., "Maturation of Poorly Crystalline Synthetic and Biological Apatites," Hydroxyapatite and Related Materials pp. 181–187 (Brown and Constantz, Editors, CRC Press, 1994).

Rev. et al., "Non–apatitic Environments in Ca–P Biominerals: Implications in Reactivity of the Mineral Phase and its Interactions with the Organic Matrix Constitutents," *Bulletin de l'Institut oceanographique, Monaco* n° special 14,1:55–64 (1994).

Rey, et al.,"The Carbonate Environment in Bone Mineral: A Resolution–Enhanced Fourier Transform Infrared Spectroscopy Study," *Calcif, Tissue Int.* 45:157–164 (1989).

Rey, et al., "Hydroxyl Groups in Bone Mineral," *Bone* 16:583–586 (1995).

Rey, C., et al., "Structural and Chemical Characteristics; and Maturation of the Calcium–phosphate Crystals Formed During the Calcification of the Organic Matrix Synthesized by Chicken Osteoblasts in Cell Culture,".

Rey and Glimcher, "Short Range Organization of the Ca–P Mineral Phase in Bone and Enamel: Changes with Age and Maturation," *Chemistry and Biol. of Mineralized Tissues* pp. 5–18 (Slavkin and Price, Editors, Elsevier Science Publishers, B.V., 1992).

Ripamonti, U., et al., "Xenogeneic osteogenin, a bone morphogenetic protein, and demineralized bone matrices including human, induced bone differentiation in athymic rats and baboons" *Matrix* 11:404–411 (1991).

Ripamonti, "Bone Induction in Nonhuman Primates, An Experimental Study on the Baboon," *Clin. Orthop,* 269:284–294 (1991).

Ripamonti, U., et al., "Growth and morphogenetic factors in bone induction: role of osteogenin and related bone morphogenetic proteins in craniofacial and periodontal bone repair," *CRC Critical Reviews in Oral Biol. Med.* 3:2–14 (1992).

Ripamonti, U., et al.,"Initiation of bone regeneration in adult baboons by osteogenin, a bone morphogenetic protein" Matrix 12:369–380 (1992).

Ripamonti, U., et al. "Induction of bone in composites of osteogenin and porous hydroxyapatite in baboons," *J. Plastic and Reconstructive Surg.* 89:731–739 (1991).

Roesgen, "The Regenerative Ability of the Lilac Crest Following Spongiosa Removal in Man–induction by Phosphate Ceramics," *Unfallchirurgle* 16(5):258–265 (Oct. 1990).

Sakae, et al., "Changes in bovine dentin mineral with sodium hypochlorite treatment," *J. Dental Res.* 1229–1234 (1988).

Santavirta, et al.,"Biocompatibility of Hydroxyapatite–Coated Hip Prostheses," *Arch. Orthop. Trauma Surg.* 110:288–292 (1991).

Schwarz et al., "Decalcified and Undecalcified Cancellous Bone Block Implants Do Not Heal Diaphyseal Defects in Dogs," *Arch. Orthop. Trauma Surg.* 111(1):47–50 (1991).

Sigholm, et al., "Graft Perforations Favor Osteoinduction, Studies of Rabbit Cortical Grafts Sterilized with Ethylene Oxide," *Acta Orthop. Scand.* 63(2):177–182 (1992).

Sinha, et al., "Surface Composition of Orthopaedic Implant Metals Regulates Cell Attachment, Spreading, and Cytoskeletal Organization of Primary Human Osteoblasts in Vitro," *Clin. Ortho.* 305:258–272 (1994).

Soballe, et al., "Histologic Analysis of a Retrieved Hydroxyapatite–Coated Femoral Prosthesis," *Clin. Orthop,* 272:255–258 (1991).

Solheim, et al., "Effect of Local Hemostatics on Bone Induction In Rats: A Comparative Study of Bone Wax, Fibrin–Collagen Paste, and Bioerodible Polyorthoester With and Without Gentamicin," *J. Biomed. Mater. Res.* 26(6):791–800 (1992).

Solheim, et al., "Inhibition of Heterotopic Osteogenesis in Rats by a New Bioerodible System for Local Delivery of Indomethacin," *J. Bone Joint Surg. (Am. )* 74(5):705–712 (1992).

Spampata, et al., "Accelerated Endochondral Osteoinduction in the Absence of Bone Matrix Particles in a Rat Model System," *J. Oral Maxillofac. Surg.* 50(2):140–151 (1992).

Spearing, et al., "Carbonated Apatite Nanocrystals from Bone," Conference Proceedings of synthesis and Processing of Nanocrystalline Powder The Mineral, Metals and Materials Society Annual Meeting (1996).

Stephenson, et al., "The Effect of Hydroxyapatite Coating on Ingrowth of Bone Into Cavities in an Implant," *J. Arthoplasty* 6:51–58 (1991).

Tochon–Danguy, et al., "Paramagnetic and Crystallographic Effects of Low Temperature Ashing on Human Bone and Tooth Enamel," *Calcif. Tiss. Res.* 25:99–104 (1978).

Umemura, et al., "Bone Inductive Activity of Hydroxyapatite–Bone Morphogenetic Protein Complex," *Nippon Shishubyo Gakkai Kalshi* 31(3):860–869 (1989).

Vaughn, et al., "Clinical and Radiographic Experience with a Hydroxyapatite–Coated Titanium Plasma–Sprayed Porous Implant," *Dent. Clin. North Am.* 36(1):263–72 (1992).

Wu, Ph.D., thesis M.I.T., "Solid state NMR study of bone mineral," (Aug. 1992).

Wu, et al., "Enhanced Osteoinduction by Intramuscular Grafting of BMP–Beta–TCP Compound Pellets Into Murine Models," *Arc. Histol. Cytol.* 55(1):97–112 (1992).

Wu, et al., "A Unique Protonated Phosphate Goup in Bone Mineral Not Present in Synthetic Calcium Phosphates," *J. Mol. Biol.* 244:423–435 (1994).

Yasko, A.W., et al., "Comparison of recombinant human BMP–2 versus cancellous bone to heal segmental bone defects," *Thirty Ninth Annual Meeting, Orthopaedic Research Society* 18:100 (1993).

Zetti–Schaffer, et al., "Scanning Electron Microscopy of Bone Ingrowth Into 40% and 80% Porous Coated AML Prostheses Retrieved at Autopsy," *Thirty Ninth Annual Meeting, Orthopaedic Research Society* 18:471 (1993).

FIGURE 1

ISOLATION OF THE CALCIUM-PHOSPHATE CRYSTALS OF BONE

This is a continuation application of U.S. Ser. No. 08/409,755, filed Mar. 24, 1995, which issued as U.S. Pat. No. 5,565,502 on Oct. 15, 1996, which is a continuation-in-part of U.S. Ser. No. 08/036,412, filed Mar. 24, 1993, issued as U.S. Pat. No. 5,439,951 on Aug. 8, 1995. This continuation application claims priority under 35 U.S.C. § 119 to PCT/US94 03214, filed Mar. 24, 1994 by Children's Medical Center Corporation.

BACKGROUND OF THE INVENTION

The present invention is generally in the area of purification of the naturally produced biological apatite crystals of bone, and of highly purified, calcium-phosphate apatite crystals of bone produced by these methods.

Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure $Ca_{10}(PO_4)_6(OH)_2$ or hydroxyapatite that is impure, containing other ions such as carbonate, fluoride, chloride for example, or crystals deficient in calcium or crystals in which calcium is partly or completely replaced by other ions such as barium, strontium and lead. Essentially none of the geological and biological apatites are "pure" hydroxyapatite since they contain a variety of other ions and cations and may have different ratios of calcium to phosphorous than the pure synthetic apatites. In general, the crystals of pure synthetic apatites, geological apatites and many impure synthetically produced apatites are larger and more crystalline than the biological crystals of bone, dentin, cementum and cartilage.

The calcium-phosphate (Ca—P) crystals of the bones of essentially all vertebrates have the basic crystal structure of hydroxyapatite $[Ca_{10}(PO_4)_6(OH)_2]$ as determined by x-ray diffraction. Indeed, the calcium-phosphate (Ca—P) crystals of essentially all of the normally mineralized tissues of vertebrates, including enamel, dentin, cementum, and calcified cartilage, have the same general crystal structure. There are few exceptions, notably the enamel of shark teeth which have fluoride ions substituted for many of the hydroxyl groups.

However, the crystals of Ca—P found in biological tissues such as bone also contain other atoms and ions such as acid phosphate groups ($HPO_4^{-2}$), and carbonate ions ($CO_3^{-2}$), which do not occur in pure, synthetic hydroxyapatite. There is also good evidence that bone crystals either do not contain hydroxyl groups, or contain only very few such groups (Bonar, et al., "Structural and composition studies on the mineral of newly formed dental enamel: a chemical, x-ray diffraction, and $^{31}P$ and proton nuclear magnetic resonance study" J. Bone Min. Res. 6:1167–1176 (1991)), and is therefore more appropriately referred to as "apatite" rather than "hydroxyapatite". Moreover, many of the carbonate and phosphate groups in bone crystals are, from the structural and physical chemical points of view, unstable and very reactive, thus providing certain physical chemical and biological functional and chemical features important in the formation and dissolution of the crystals in biological tissues.

Recent important $^{31}P$-nuclear magnetic resonance spectroscopy studies have also demonstrated that the short-range order or environment of the $HPO_4^{-2}$ groups in bone crystals are distinctly different than the $HPO_4^{-2}$ groups in synthetic apatites and other related calcium-phosphate crystals (Wu, Ph.D. thesis M.I.T., "Solid state NMR study of bone mineral", August, 1992). These differences in chemical, structural, and short range order of the bone crystals compared with pure, synthetic hydroxyapatite also reflect significant differences in their reactivity and hence in their potential function in a biological environment.

The crystals of bone, dentin and cementum are very small, irregularly shaped, very thin plates whose rough average dimensions are approximately 10 to 50 angstroms in thickness, 30 to 150 angstroms in width, and 200 to 600 angstroms in length. This results in their having a very large surface area to present to the extracellular fluids which is critically important for the rapid exchange of ions with the extracellular fluids. This "ion-reservoir" function of the inorganic crystals is very important for a number of critical biological functions.

The vast majority of the Ca—P crystals of bone are located within the collagen fibrils of bone, as reported by Glimcher, M. J., "A basic architectural principle in the organization of mineralized tissues" in: Milhaud, A. G., ed. Proceedings of the Fifth European Symposium on Calcified Tissues, Bordeaux, France, 1968, Lee and Glimcher, "Three-dimensional spatial relationship between the collagen fibrils and the inorganic calcium phosphate crystals of pickerel (*Americanus americanus*) and herring (*Clupea harengus*) bone", J. Mol. Biol. 217: 487–501 (1991); and Glimcher M J, "Molecular biology of mineralized tissues with particular reference to bone" Rev. Mod. Physics 31:359–393 (1959). In general, bone contains approximately 35% organic constituents, the major component being collagen fibrils. See, for example, Cohen-Solal, et al., "Identification of organic phosphorus covalently bound to collagen and non-collagenous proteins of chicken-bone matrix: the presence of O-phosphoserine and O-phosphothreonine in non-collagenous proteins, and their absence from phosphorylated collagen" Biochem. J. 177:81–98 (1979). Due to their intimate physical location and interrelationship with the collagen fibrils, it has not heretofore been possible to separate and isolate the crystals of bone from the collagen fibrils of bone and other organic constituents of the tissue without producing significant changes in the chemistry, structure, degree of crystallinity and size of the crystals, as reported by Sakae, et al., "Changes in bovine dentin mineral with sodium hypochlorite treatment, J. Dental Res. 1229–1234 (1988).

Methods previously used to remove and isolate the calcium-phosphate apatite crystals of bone have not been successful, either because they do not completely separate the crystals from the organic constituents and/or because they alter the chemistry and structure of the crystals. For example, hydrazine treatment of well mineralized bone carried out at temperatures of 50° C. and higher yielded crystals containing significant amounts of organic constituents and induced significant changes in the crystals. Similarly, while substances such as sodium hypochlorite released calcium-phosphate apatite crystals from bone and other tissues, it was used in the form of an aqueous solution. Contact of bone crystals with water for even short periods of time has been shown to significantly alter the crystals by dissolution, reorganization, re-precipitation, and cannot be prevented by adding calcium and phosphate ions to the water based solution. See, for example, Landis, et al., "Electron microscopic observations of bone tissues prepared by ultracryomicrotomy" J. Ultrastruct. Res. 59:185–206 (1977); Landis, et al., "Electron microscopic observations of bone tissue prepared anhydrously in organic solvents" *J. Ultrastruct. Res.* 59:1–30 (1977); and Landis, et al., "Electron diffraction and electron probe microanalysis of the mineral phase of bone tissue prepared by anhydrous techniques" *J. Ultrastruct. Res.* 63:188–223 (1978). Furthermore, it has been found that the crystals are not only altered but also contain significant amounts of organic matrix. In a similar fashion, plasma ashing of bone to remove the organic matrix and disperse the crystals has been shown to induce major alterations in the crystal which as in the other methods described above can also contain significant amounts of organic constituents. Such treatment seriously alters the chemistry and structure of the crystals.

The synthetic materials are highly diverse, as reported in the literature. For example, the characterization of four commercial apatites was reported by Pinholt, et al., *J. Oral Maxillofac. Surg.* 50(8), 859–867 (August 1992); *J. Cariofac. Surg.* 1(3), 154–160 (July 1990) reports on a protein, biodegradable material; Pinholt, et al., *Scand. J. Dent. Res.* 99(2), 154–161 (April 1991) reports on the use of a bovine bone material called Bio-Oss™; Friedman, et al., *Arch. Otolaryngol. Head Neck Surg.* 117(4), 386–389 (April 1991) and Costantino, et al., *Arch. Otolaryngol. Head Neck Surg.* 117(4), 379–384 (April 1991) report on a hydroxyapatite cement; Roesgen, *Unfallchirurgle* 16(5), 258–265 (October 1990), reports on the use of calcium phosphate ceramics in combination with atogeneic bone; Ono, et al., *Biomaterials* 11(4), 265–271 (May 1990) reports on the use of apatite-wollastonite containing glass ceramic granules, hydroxyapatite granules, and alumina granules; Passuti, et al., *Clin. Orthop.* 248, 169–176 (Nov. 1989) reports on macroporous calcium-phosphate ceramic performance; Harada, *Shikwa-Gakuho* 89(2), 263–297 (1989) reports on the use of a mixture of hydroxyapatite particles and tricalcium phosphate powder for bone implantation; Ohgushi, et al., *Acta Orthop. Scand.* 60(3), 334–339 (1989) reports on the use of porous calcium phosphate ceramics alone and in combination with bone marrow cells; Pochon, et al., *Z-Kinderchir.* 41(3), 171–173 (1986) reports on the use of beta-tricalcium phosphate for implantation; and Glowacki, et al., *Clin. Plast. Surg.* 12(2), 233–241 (1985), reports on the use of demineralized bone implants. No general conclusions can be drawn from these representative reports except that the need for materials which are useful in fixation of implants and in repair or replacement of bone defects remains and that the materials now available do not solve the many problems associated with the treatment of these problems, due to many variables, including the properties of the materials as well as the ease with which they can be manufactured and utilized by the surgeon.

The majority of synthetic hydroxyapatite preparations that have been proposed for use as bone inductors (to induce bone formation) and osteoconductors (by acting as scaffolds to facilitate for the continuous progression of new bone formation) are of synthetic origin and distinct structurally and chemically from the biological calcium-phosphate crystals in bone. All of these apatites are not only chemically and structurally distinct from the apatite crystals of bone, especially in their short range order, size and reactivity, but in some cases, they contain varying amounts of amorphous calcium-phosphate, that is, calcium-phosphate solids which are not crystalline at all. In other instances, the calcium-phosphates made synthetically also contain calcium salts other than apatite crystals such as calcium oxides. To date, it has not been shown how these additional calcium salts are biocompatible or without untoward effects, either biologically or structurally, nor how they affect the bonding strength between the synthetic apatites used to coat the surfaces of artificial joints implanted to bone and the surface of the artificial joint, and between the synthetic apatites and the bone into which the device is implanted.

It is therefore an object of the present invention to provide the biologically, naturally formed crystals of bone a purified apatite that are substantially free of organic material but which also consist predominantly of highly uniform crystals with respect to the chemistry, structure, size, shape and index of crystallinity.

It is a further object of the present invention to provide methods for the further purification of bone apatite crystals that remove essentially all organic material without disrupting the natural crystalline structure of the bone crystals.

SUMMARY OF THE INVENTION

The present invention is a process for removing and isolating the calcium-phosphate crystals of bone from a substantial amount of the organic matrix and cellular constituents of bone without significant physical, chemical or structural alterations in the crystals. The crystals can be isolated from bone, cementum, dentin, enamel, and cartilage (referred to collectively herein as "bone"). The crystals can then be further treated to remove the remaining amount of organic material associated with the crystals, leaving them essentially free of any of the organic constituents of bone, without significant physical, chemical or structural alterations in the crystals, that is, having the same chemical composition, structure, short range order (as measured using standard techniques), and index of crystallinity as the native bone from which it is derived.

Critical elements in the process are the use of non-aqueous solvents, maintainance of low temperatures, less than room temperature, preferably in the range of 2° to 4° C., or lower, for example, the temperature of liquid nitrogen, and the avoidance of techniques inducing changes in the crystal structure or chemistry, such as high power sonication or grinding at warm temperatures. The process includes three steps: (1) degradation and extraction of the organic matrix constituents, (2) disaggregation of bones after organic matrix degradation, and (3) separation of single crystals from small aggregates of crystals. The calcium-phosphate (Ca—P) crystals (also referred to as "apatite") of bone are initially separated from the highly dense connective tissue in bone, by a combination of reaction with a polar solvent such as hydrazine at low temperatures at a ratio of 10 mls solvent to 100 mg bone, ultrasonication for example, for 2 to 3 minutes over 30 to 60 minutes over a period of twelve hours at 270 watts and 63 kHz), and/or plasma ashing at low power (for example, 5–10 watts for 5 to 15 minutes). In the second step, the bones are disaggregated using hydrazine or low power plasma ashing, followed by suspension in a non-aqueous solvent such as 100% ethanol at a low temperature, between 2° and 4° C., and ultrasonication, for example, at 270 watts and 63 kHz for 2 to 3 minutes, every 30 to 60 minutes for 12 hours. The small aggregates of crystals are separated from single crystals by centrifugation, for example, at 1,000 g for 10 minutes. Ultracentrifugation, for example, for 30 minutes at 30,000 g, can be used to form a supernatant consisting essentially of single crystals in suspension. Ultrasonication and/or plasma ashing can be used to recycle the aggregates present in the precipitate.

These procedures yield isolated crystals free of collagen fibrils even from adult, heavily calcified, mature bone. The crystals have the signature characteristics of bone crystals in native bone, both analytically, chemically and structurally.

Transmission electron microscopy reveals well dispersed crystals, free of any observable collagen fibrils or any other organic material. Chemical analysis, x-ray diffraction, and Fourier transform infrared spectroscopy show the typical characteristics of the crystals in native bone, including the presence of carbonate and acid phosphate groups, and the absence of hydroxyl groups as detected by Fourier transform infrared spectroscopy and proton nuclear magnetic resonance spectroscopy.

The isolated calcium-phosphate crystals are useful in a variety of applications, including chromatographic separation and isolation of proteins and in medical or therapeutic applications, such as in the healing and repair of bone, the replacement of bone with the eventual formation of new bone in the defects, and, in general, in the induction of new bone and in the osteoconductive progression of new bone formation, including the coating of specific surfaces of artificial joints or teeth implanted in bone.

DETAILED DESCRIPTION OF THE INVENTION

As used herein, "purified" and "purification" are not terms which are used to suggest that the apatite crystals are synthesized de novo in vitro; rather they refer to procedures to remove, disperse and isolate the natural, native, biological crystals which are in bone from bone, cementum, enamel, dentin and cartilage, without significantly altering their physical shape, size, structure or chemistry. They can be prepared so that their dry weight contains roughly as little as 25% or less of the total dry weight as organic matrix constituents or be further subjected to procedures which remove more of the organic constituents so that as little as approximately 2% or less of their dry weight is accounted for by organic constituents.

The exact determination of the size and habit of the extremely small calcium-phosphate (Ca—P) crystals in bone, and their short range order and fine structure, has been hampered because the crystals are embedded principally within collagen fibrils, which themselves are densely packed into fibers and fiber bundles of the highly organized extracellular matrix of the tissue fabric. Previous attempts to isolate the crystals free of the collagen fibrils and other organic matrix constituents by reaction with hydrazine and other reagents or by plasma ashing have left variable but significant quantities of organic matrix in the samples and have produced readily detectable and significant changes in the crystals.

Figure 1:
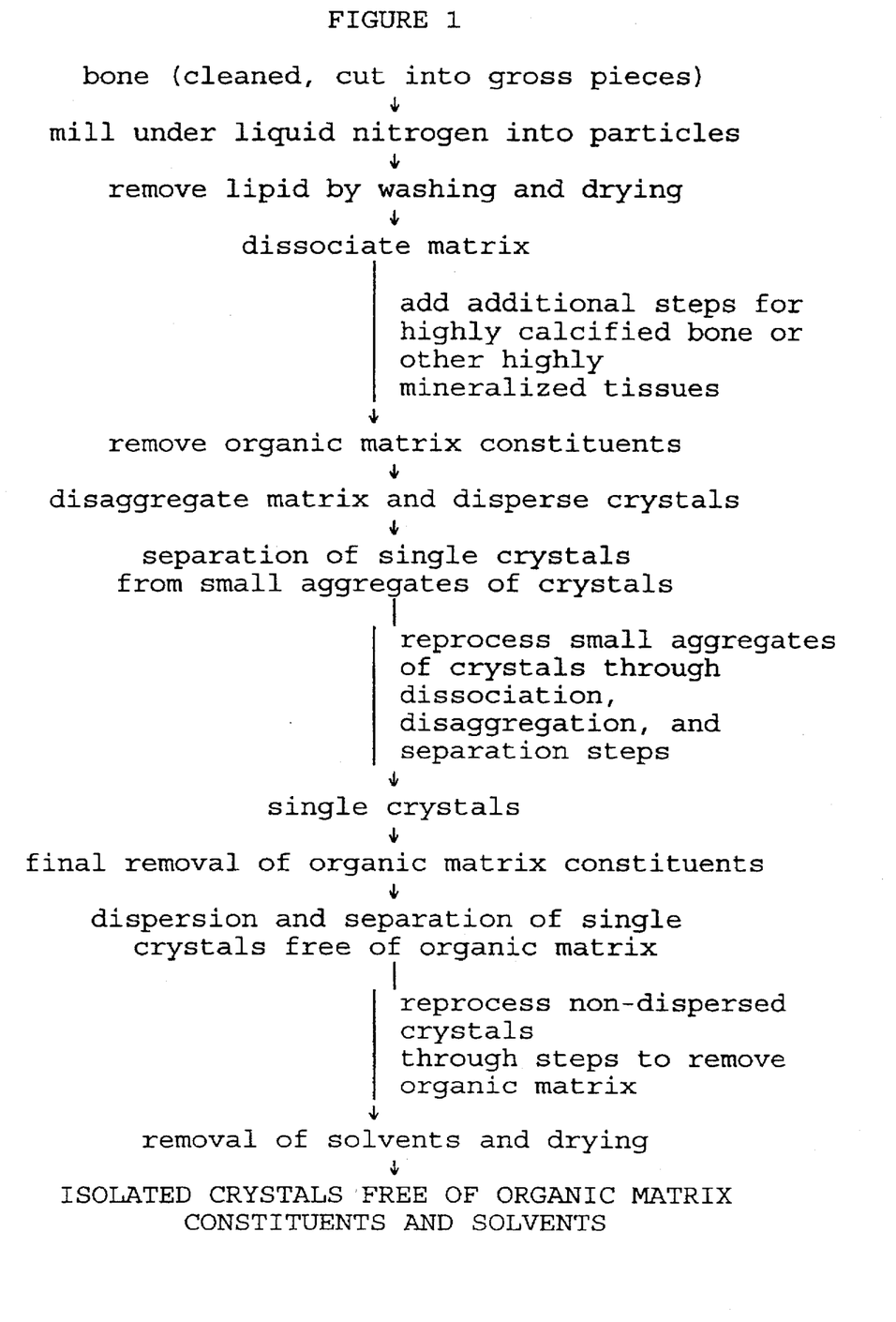
FIG. 1 is an abbreviated schematic flow chart of a general method for the separation and isolation of calcium-phosphate crystals from young, poorly mineralized bone (I) or more mature, more heavily mineralized bone (II).

Bone mineral crystals are isolated by a combination of a series of techniques which disaggregate the bone matrix and facilitate additional methods which remove the organic matrix constituents, and which permit the dispersion of single crystals and small aggregates of crystals. The final result of these processes yields the native bone crystals free of organic matrix constituents. All steps in the procedure are performed in non-aqueous conditions and at low temperature: dissociation of matrix at less than 36° C., removal of matrix at between 2° and 4° C. with a non-aqueous solvent such as hydrazine or 100% ethanol, plasma ashing at low temperature, and dispersion and separation of the crystals at less than 10° C. The methods described herein are shown schematically in FIG. 1, where (I) is the preferred process for use with young, not highly mineralized bone, and (II) is the preferred processes for use with more mature, and more mineralized bone. A combination of several of the above techniques can also be used depending on the level of mineralization of the tissue, the density of packing in the tissue, and other variables.

Isolation and Characterization of Calcium-Phosphate Crystals from Bone

A method has been developed to remove and isolate the calcium-phosphate apatite crystals from bone that yields calcium-phosphate crystals that are essentially completely free of organic material and which have been shown not to have been significantly altered with regard to their structure or chemistry. As used herein, "bone" includes other biological sources of calcium-phosphate crystals including dentin, enamel, cementum and cartilage. "Purified" means separating and isolating the naturally occurring biological crystals in bone away from the organic matrix constituents, especially collagen fibrils, to less than 25%, most preferably less than 1%, of their total dry weight. The same procedures can be applied to other biologically calcified tissues such as the exoskeletons of invertebrates like coral which contain crystals of calcium carbonate. This material has also been used in combination with repair or replacement of bone.

There are three principal stages in the purification and isolation of the crystal: (1) degradation and extraction of organic matrix constituents; (2) disaggregation of bone crystals after the initial step of degradation of the organic matrix; and (3) separation of single crystals from small aggregates of crystals. The initial separation of the crystals of bone is accomplished by dissociation of bone matrix constituents; decomposition of organic matrix constituents; disaggregation of dissociated bone matrix and the decomposed organic matrix; dispersion of single crystals and small aggregates of crystals; separation of single crystals; and removal of solvents. Importantly, none of the reagents or procedures used in processing of the crystals can include water. This is in contrast with other reported methods, for example, using sodium hypochlorite as a water based solution.

Degradation and Extraction of Organic Matrix

The following procedures are described separately, but may be used in combination or alone, depending on the starting material.

a. Preparation of bone particles

Bone powder is prepared by mill grinding fresh bone in liquid nitrogen and sieving to a particle size ranging up to approximately 200 microns, preferably 75 to 200 microns. The exact total times for mill-grinding the bone to a suitable particle size in liquid nitrogen which is critical to the process depends on the mass of bone used, the size of the gross pieces, and the density of the bone. In any case, milling must be done in short pulses, for example, of 5 to 15 seconds for small quantities of bone powder (50 mg), and for not too long a total time. One must monitor the specific processes for the specific type of bone, the amount of bone, and so forth, by transmission electron microscopy to make certain that processing has not caused changes in either the size, shape, or physical and chemical characteristics of the crystals.

When these techniques are used with more calcified and mature bone, however, the yield of dispersed crystals is less than that obtained from the younger, less heavily mineralized bone. A second procedure with a higher yield of isolated, dispersed crystals free of collagen fibrils and other organic constituents as observed by electron microscopy, can be obtained even from mature, normally calcified bone. This technique was developed based on observations that both aggregates of isolated crystals free of collagen fibrils and particles composed of aggregates of collagen and apatite crystals could be dispersed and separated from one another when they were gently sonicated for short periods of time in cold, organic polar solvent such as 100% ethanol using low energy sonication. In this procedure, the diaphyses of fresh long bones cleaned of periosteum and cartilage are frozen in liquid nitrogen, cut into gross pieces, and cleaned endosteally. The pieces of bone are ground in a mill in very short 5 to 30 second pulsed bursts in liquid nitrogen to a particle size of up to approximately 200 microns, preferably 75 to 200 microns. Total grinding time depends on the size of the initial gross pieces and the density of the bone (e.g., adult bovine bone compared with young chicken bone or small flexible fish bones).

b. Dissociation of bone matrix constituents and Decomposition of organic matrix constituents.

The dehydration and chemical dissociation of the bone matrix constituents facilitates the disaggregation of the bone matrix by mechanical force, for example, by sonication.

The dried bone powder is suspended in an organic solvent such as hydrazine or ethanol precooled to just above its freezing temperature, in a container jacketed to maintain the low temperature of the solvent and bone powder. Particles are subjected to several low power sonications, each period lasting up to 10 minutes, depending on the volume of solvent and the total mass of bone powder utilized, in order to disaggregate the dissociated bone matrix and the decomposed matrix and release single crystals and small aggregates of crystals. The ultrasonic disaggregation is carried out in a non-aqueous organic solvent such as hydrazine, ethanol, methanol, or other solvent with similar dielectric properties at 10° C. or lower. This procedure can be repeated a number of times.

In a preferred embodiment, the disaggregated materials are treated with a polar non-aqueous solvent such as hydrazine ($NH_2$—$NH_2$) for varying periods of time at low temperatures, preferably less than 6° C., depending on the selection of solvent, most preferably between 2° and 4° C. for hydrazine, for a period of time such as 12 hours, using a ratio equivalent to 10 ml solvent/100 mg bone powder. Reaction of the bone with hydrazine for 12 hours, at a ratio of 10 ml hydrazine/100 mg of bone powder, at a low temperature, for example, between 2° and 4° C., in combination with ultrasound every 30 to 60 minues for a period of two to three minutes at 270 watts, 63 KHz, peak output frequency, is particularly effective. At the end of each 12 hour extraction, the powder is thoroughly washed and re-extracted with 100% ethanol or equivalent solvent at low temperature.

Suspending the bone particles in 100% methanol saturated with either sodium dodecyl sulphate (SDS), guanidine hydrochloride (GuHCl), or other non-aqueous solutions of organic detergents or dissociative compounds enhances disaggregation by decreasing forces between molecules in the matrix and thereby enhances the disaggregation of the matrix. The bone particles are washed with 100% methanol or ethanol afterwards to remove any residual detergent.

Single crystals and small aggregates of crystals are released from the bone matrix following hydrazine treatment by washing in an organic solvent such as ethanol or methanol at a temperature of 10° C. or less and dried by ether or ethyl acetate extraction. Critical point drying using $CO_2$ after replacing absolute ethanol enhances the rate of dehydration and enhances the disaggregation of the matrix.

Transmission electron microscopy of a low speed ultracentrifuged supernatant from relatively young bone treated with hydrazine reveals dispersed crystals of similar size and shape to the Ca—P crystals observed in bone as well as collagen fibril-crystal aggregates, which can then be removed by high speed centrifugation, leaving only the dispersed crystals free of collagen fibrils as observed by electron microscopy. Following low speed centrifugation, the crystals in the supernatant are separated from the solid bone particles, resuspended in an organic solvent such as ethanol and thoroughly washed, centrifuged and filtered in cold ethanol or other equivalent solvent.

c. Disaggregation and Dispersion

The single crystals and small aggregates of crystals are treated with low power plasma ashing for short periods of time (five to fifteen minutes at 5 to ten watts) and then dispersed in organic solvents such as ethanol, methanol or other solvents of similar dielectric properties. Treatment with low power plasma ashing for short periods of time assures that the single crystals and small aggregates of crystals are dispersed into the solvent. Apparatus are commercially available for plasma ashing, for example, the LTA-302 model from Anatech, Ltd., Fitzwilliam, N.H. The procedure may be repeated three to five times, or more, depending on the extent of mineralization. It is particularly useful to disaggregate and dissociate the crystals and organic matrix in young, not fully mineralized or fully compacted dense bone. Crystals and crystal aggregates released directly by plasma ashing of bone particles (equivalent to 10 to 50 watts, five hours) at low temperatures can also be dispersed in ethanol, methanol or equivalent solvents. This can be again treated with plasma ashing to remove any residual organic solvents as well as any residual organic matrix constituents. The process may need to be repeated over a period of at least 15 hours or more in period of three to five hours to prevent heating.

Disaggregation of Bone Crystals

The residue from either the hydrazine or low power plasma ashing is suspended in an organic solvent such as 100% ethanol, at a ratio of 1 ml solvent/100 mg crystals, at a low temperature of between 2° and 4° C., then subjected to ultrasonication every two to three minutes for every 30 to 60 minutes for 12 hours, using power equivalent to 270 watts, 63 kHz peak output frequency. This disperses the crystals as individual single crystals and small aggregates of individual crystals.

Separation of Single Crystals from Aggregates

Single crystals dispersed in ethanol, methanol or equivalent solvents remain in the supernatant when subjected to a force of under 1,000 g for about ten minutes, whereas small aggregates of crystals are present in the pellet. After separating single crystals from aggregates, the single crystals are harvested by centrifugation at 30,000 g for 30 minutes. The small crystal aggregates can then be processed through the disaggregation and separation procedures to obtain additional single crystals.

The single crystals are washed in a solvent such as ethanol, followed by washing with ethyl acetate to remove the ethanol, drying by passing dry $N_2$ gas over the crystals and vacuum evaporating.

Additional hydrazine and intermittent ultrasonication and/or low power plasma ashing can be used to completely remove any solvents that may remain bound to the crystals. This procedure insures that the crystals are solvent free as well as free of organic matrix constituents.

Characterization of Calcium-Phosphate Crystals Obtained in Initial Separation After the first two steps, the crystals still have associated with them some residual organic constituents or breakdown products of the organic constituents, as shown by analytical chemical analyses, although electron microscopy reveals only the apatite crystals and no collagen fibrils or other organic components.

Hydrazine reaction with young bone followed by sonication in organic polar solvent yield isolated crystals free of collagen fibrils by electron microscopy. The crystals are then thoroughly washed a number of times. As an additional step to remove the residual organic material remaining on the crystal surfaces, the crystals are treated by low energy plasma ashing (for small quantities of bone, approximately 5 mg, with low power defined as one watt or less, for 5 hours).

Chemical analysis, x-ray diffraction and Fourier transform infrared spectroscopy (FT-IR) of the crystals show no significant differences from analyses of whole, native bone, including the presence of carbonate and acid phosphate groups, and the failure to detect hydroxyl groups by fourier transform infrared spectroscopy and proton-nuclear magnetic resonance spectroscopy, signature characteristics of native, bone apatite crystals. Further analysis was done using amino acid analysis to determine the amount of protein associated with the isolated bone crystals, and atomic absorption spectroscopy to measure calcium, phosphorus, and carbonate. The long-range order was determined by powder x-ray diffraction using CU K$\alpha$-radiation. Electron diffraction was done using an electron microscope with a liquid nitrogen cooling device.

The results indicate that there was no change in the composition of the isolated crystals as compared with the compositions of native bone, and that it was possible to remove essentially all of the organic matrix constituents from the crystals. X-ray diffraction of the isolated crystals showed typical, poorly crystalline apatite, similar to powdered intact bone. No crystalline phase other than apatite was noted in any of the samples. No structural changes were noted as a result of the isolation procedure. TEM of control crystals isolated by ethanol and sonication, without treatment with any of the procedures used to degrade and remove the organic constituents, shows no difference in crystal habit and size as compared with those treated to remove the organic constituents. The crystal habit is thin plates, with no rod or needle-like crystals. The major inorganic constituents of isolated crystals were calcium and phosphorus. There was little variation in the average dimensions of width and length of the crystals, with the thickness of at least some of the crystals being no more than 1.5 to 2.0 nm. This was a function of source, with larger crystals obtained from bovine bone as compared with those of mouse and chicken bone, and longer relative lengths when obtained from fish bone. FTIR showed no interference by organic constituents, providing a very clear and distinct spectrum of a carbonate apatite containing $HPO_4^{-2}$ groups.

The chemical analysis for bovine bone and crystals isolated from bovine bone is: native bone, 1.62 Ca/P (molar); 6.4% $CO_3$; and 28.6% protein; crystals, 1.63 Ca/P (molar); 5.6% $CO_3$; and <0.1% protein. The average dimensions of crystals isolated by ethanol alone, and after removal of organic constituents were 15.6±7.3 nm wide, 27.3±11.4 nm long, and 0.59±0.18 width/length and 15.8±7.2 nm wide, 27.3±11.2 nm long, and 0.59±0.17 width/length, respectively. Computer enhanced Fourier transform infrared spectroscopy analyses of native bovine bone and isolated crystals show 0.40 labile $PO_4$, 0.76 $PO_4$ resolution factor (RF), 0.50 labile $CO_3$, and 0.53 $v_2$ $CO_3$ RF, and 0.3 labile $PO_4$, 0.79 $PO_4$ RF, 0.48 labile $CO_3$, and 0.54 $v_2$ $CO_3$ RF, respectively.

Applications for Purified Calcium-Phosphate Crystals

Chromatographic Separations Applications

The isolated bone crystals can be used to purify and isolate biological molecules such as proteins, glycoproteins, carbohydrates, and nucleotides, by standard chromatographic and other analytical and preparative technologies. Synthetic apatites are already used for chromatography but performance varies from batch to batch and from producer to producer, depending on how the synthetic apatites are made, sized, and so forth.

The Ca—P crystals isolated as described herein are more uniform in size, chemical composition, and structure from the synthetic apatites, and differ from synthetic apatites because they have certain specific functional groups such as carbonate and acid phosphate moieties in specific locations and at specific energy levels as well as small amounts of other ions, many of which are on the surfaces of the crystals and in the case of bone crystals, for example, no detectable hydroxyl groups. Accordingly, they should provide more reproducible separations of specific components from a mixture of many components and also may be able to more selectively separate specific molecules originally present in the organic matrix of tissues such as bone and tooth with which they have specifically interacted in the native tissue as a result of these unique chemical and structural characteristics of the native bone crystals.

Therapeutic Applications

The purified calcium-phosphate crystals isolated from bone are useful as an aid to induce and promote bone healing. Synthetic apatite crystals have been shown to be biocompatible, both in vivo and in bone cell (osteoblast cell) cultures (Cordoba, et al., "Effect of microcrystalline hydroxyapatite on bone marrow stromal cell osteogenesis", Thirty Ninth Annual Meeting, Orthopaedic Research Society, 1993). There is also experimental evidence that synthetic apatite preparations can act as osteoinductors, biologically active materials which induce cells to form bone, and osteoconductors, biologically active materials which facilitate and provide a scaffolding on which bone formation can spread and advance.

Accordingly, the crystals have a variety of therapeutic applications, either alone or in conjunction with other substances bound to the crystals such as, for example, other bone cell inducers and stimulators, including the general class of cytokines such as the TGF-β superfamily of bone growth factors (Cytokines and Bone Metabolism, Gowen, ed (CRC Press, 1992)), the teachings of which are incorporated by reference herein, (available from Boehringer-Mannheim), the family of bone morphogenetic proteins, osteoinductors, and/or bone marrow or bone forming precursor cells, isolated using standard techniques. With reference to sources and amounts of various materials that can be included with the crystals, see, for example, Glowacki, J., et al. "The role of osteocalcin in osteoclast differentiation" J

*Cellular Biochem* 45:292–302 (1991); Ballock, T. T., et al. "Regulation of collagen expression in periosteal cells by three members of the TGF-B superfamily" *Thirty Ninth Annual Meeting, Orthopaedic Research Society;* 18,734 (1993); Ripamonti, U., et al. "Induction of bone in composites of osteogenin and porous hydroxyapatite in baboons" *J. Plastic and Reconstructive Surg.* 89:731–739 (1991); Ripamonti, U., et al. "Growth and morphogenetic factors in bone induction: role of osteogenin and related bone morphogenetic proteins" *CRC Critical Reviews in Oral Biol. Med.* 3:1–14 (1992); Ripamonti, U., et al. "Initiation of bone regeneration in baboons by osteogenin, a bone morphogenetic protein" *Matrix;* 12:40–55 (1992); Ripamonti, U., et al. "Xenogeneic osteogenin and demineralized bone matrices including human induced bone differentiation in athymic rats and baboons" *Matrix* 11:404–411 (1991); Cook, S. D., et al. "Restoration or large diaphyseal segmental defects in rabbits using recombinant human osteogenic protein (OP-1)" *Combined meetings of Orthopaedic Research societies of USA, Japan and Canada* 1, 66 (1991); Miyamoto, S., et al. "Trans-filter bone induction in monkeys by bone morphogenetic protein" *Thirty Ninth Annual Meeting, Orthopaedic Research Society* 18, 99 (1993); Yasko, A. W., et al. "Comparison of recombinant human BMP-2 versus cancellous bone to heal segmental bone defects" *Thirty Ninth Annual Meeting, Orthopaedic Research Society* 18, 100 (1993); Aspenberg, P., et al. "Bone morphogenetic protein induces bone in the squirrel monkey, but bone matrix does not" *Thirty Ninth Annual Meeting, Orthopaedic Research Society* 18, 101 (1993); Iwasaki, M., et al. "Bone morphogenetic protein-2 stimulates osteogenesis in high density culture of periosteum-derived cells" *Thirty Ninth Annual Meeting, Orthopaedic Research Society* 18, 483 (1993); Cook, S. D., et al. "Recombinant human osteogenic protein-1 (rhOP-1) heals segmental long-bone defects in non-human primates" *Thirty Ninth Annual Meeting, Orthopaedic Research Society* 18, 484 (1993); and Hunt, T. R., et al. "Healing of a segmental defect in the rat femur using a bone inducing agent (BIA) derived from a cultured human osteosarcoma cell line (SAOS-2)" *Thirty Ninth Annual Meeting, Orthopaedic Research Society* 18, 489 (1993), the teachings of which are incorporated by reference herein. The crystals can also be mixed with antibiotics or chemotherapeutic agents.

The isolated calcium-phosphate crystals are useful as an aid in the healing of bone defects, fractures, and other similar situations, or in the treatment of local bone resorption such as occurs in periodontal tissue or in the fixation of prosthetic implanted teeth into the bony jaws, especially when combined with substances which inhibit or lessen bone resorption such as isoleukin 1-β, for example, and osteoinductors such as the family of TGF-β. The crystals can be applied as a cement, in combination with a binder, preferably a biodegradable polymeric matrix, although non-biodegradable polyacrylate and cyanoacrylates are also useful, or as a paste. They can be sprayed or otherwise applied to the surface of prosthetics prior to or at the time of implantation, using in combination with an adhesive applied to the surface of the implant. They can also be used as filler in gaps in the bone resulting from trauma, infection, or cancer, using other materials to serve as structural supports until the crystals are replaced by newly formed bone. See, for example, Aberman, H. M., et al. "Gap healing in a non-weight bearing dog model: effectiveness of a solution precipitated apatite coating". *Thirty Ninth Annual Meeting, Orthopaedic Research Society* 18, 466 (1993).

A major complication of the use of artificial skeletal joints as implants and prosthetic teeth as implants in the loosening of artificial joint and tooth prostheses implanted into bone is due to bony resorption about the implant. Examination of the surrounding tissues and prostheses has shown that this is due to the formation of cellular reactive connective tissue which forms after implantation and which incites resorption of the bone. This in turn is felt to be due for the most part to excessive micromotion between the implant and the living bone into which it is placed, presumably due to failure of sufficient interface appositional strength between the bone surface and the prosthesis. Recent work has also shown that when the appositional surfaces of the prosthesis are coated with apatite crystals, there is a significant increase in the appositional strength between the prosthetic surface and the implant and the surface of the bone which greatly diminishes the micromotion between the two components. See, for example, Bragdon, C. R., et al. "The histology of bone ingrowth at the implant/bone interface under known amounts of micromotion" *Thirty Ninth Annual Meeting, Orthopaedic Research Society* 18, 468 (1993); Burke, D. W., et al. "Mechanical aspects of the bone-porous surface interface under known amounts of implant motion: an in vivo canine study" *Thirty Ninth Annual Meeting, Orthopaedic Research Society* 18, 470 (1993); and Hollis, M. J., et al. "Effect of micromotion on ingrowth into porous coated implants" *Thirty Ninth Annual Meeting, Orthopaedic Research Society* 18, 472 (1993).

The crystals can be used in powdered form, shaped into blocks of ceramic, porous coatings, or mixed with other materials for use as coatings or cements, using the methods and materials known to those skilled in this art. These are then useful for the manufacture of artificial prostheses, coatings on artificial joints or implanted prosthetic teeth and using the biological bone crystals embedded and combined with a biodegradable carrier. Components which induce bone formation and others which diminish bone resorption as well as antibiotics and other chemotherapeutic agents can be combined with the apatite crystals.

To date, there is no available detailed analysis of the intricate chemistry and structure of the synthetic apatites used to coat the prostheses. Although the methods of preparation of the synthetic apatites varies, they are generally formulated and applied to the metallic surfaces of the implants by plasma spraying which results not only in the formation of crystalline hydroxyapatites (but of varying chemical composition) and what has been term "amorphous" calcium-phosphates as well as calcium salts in addition to calcium-phosphate apatites. The specific chemical and physical characteristics of the native or natural calcium-phosphate crystals of bone isolated from bone, formulated to allow for increased bone formation (i.e. bone induction) and osteoinduction should not only permit a much increased interfacial appositional strength and bond between the bony surfaces and the implanted device (joint or tooth implant) but also allow a more bony bonding between the implant and the bone into which the implant is placed.

In all of these applications, care should be taken not to alter or damage the crystals, for example, by exposure to high temperatures and water.

EXAMPLE 1

Preparation of Purified Bone Crystals

METHODS

1. Dissociation of bone matrix

Bone powder is reacted three times with absolute ethanol and three times with ether or ethyl acetate to dehydrate the bone matrix (10 ml/100 mg of bone powder). This treatment is followed by critical point drying and chemical dissociation. For the critical point drying, bone matrix is immersed in absolute ethanol, and is replaced with liquid $CO_2$ (10 ml/100 mg bone powder). The temperature is then slowly increased up to the critical point of $CO_2$ (31° C. at 72.9 atmospheres). For the chemical dissociation of bone matrix, the bone particles are reacted with saturated sodium dodecyl sulphate in methanol or other detergents or dissociative compounds in organic solvents at 20° C. which enhances the subsequent disaggregation (10 ml/100 mg of bone powder) by decreasing the forces between organic molecules in the organic matrix.

2. Removal of organic matrix constituents:

Lipid is removed from the bone powder by reaction with methanol/chloroform (1:2), or ether or ethyl acetate treatment (10 ml/100 mg of bone powder) after reaction with absolute ethanol. This procedure is repeated three or more times.

Proteins and other organic matrix constituents are removed by three extractions of bone powder or of powdered crystal (single crystals and small aggregates of crystals) with hydrazine at low temperature (2°–4° C.). Each extraction is for a period of 12 hours followed by intermittent low power ultrasonication (270 watt/63 KHz, peak-output/frequency) for less than 3 minutes. It can be also removed by the repeated low power plasma ashing (5–10 watts for 5 hrs or crystal powder at 10–50 watts for 5 hrs.)

3. Disaggregation of bone matrix

Bone powder already dissociated physically or chemically as above is disaggregated in absolute ethanol (1 ml/100 mg) by the force of low power ultrasonic force (270 watt/63 KHz, peak-output/frequency) at under 10° C. which releases single crystals and small aggregates of single crystals.

4. Dispersion of single crystals

Low power (5 watt) plasma ashing treatment of the dissociated and/or disaggregated powder for short periods of time (5 minutes) at low temperature. This makes it possible to disperse single crystals and small aggregates of crystals in solvents such as ethanol and methanol or other solvents of similar dielectrical properties.

5. Separation of single crystals from small aggregates of crystals.

Small aggregates of crystals dispersed in methanol or ethanol or other organic solvents (see above) are removed from the suspension by centrifugation at 1,000 g for 10 minutes. The single crystals which remain in the supernatant are then collected by ultracentrifugation at 30,000 g for 30 minutes.

6. Washing and drying.

The bone powder or crystals are washed in absolute ethanol (10 ml/100 mg) three times and collected by centrifugation at 10,000 g. Samples are further washed with ether or ethyl acetate three times and dried in vacuum.

7. Removal of remaining solvents.

Dried crystals are treated with low power plasma ashing (5 watts for 10 minutes at low temperature) to remove crystal bound solvents and any remaining organic matrix constituents.

We claim:

1. A composition of calcium-phosphate apatite crystals of essentially the same chemical composition, structure, short range order, and index of crystallinity as the calcium-phosphate crystals present in bone selected from the group consisting of bone, cartilage, cementum, dentin, and enamel, essentially free of collagen fibrils.

2. The composition of claim 1 containing less than 25% of the dry total weight as organic material.

3. The composition of claim 2 containing less than 1% dry total weight as organic material.

4. The composition of claim 1 wherein the crystals are irregularly shaped, very thin plates whose rough average dimensions are approximately 10 to 50 angstroms in thickness, 30 to 300 angstroms in width, and 70 to 600 angstroms in length.

5. The composition of claim 1 further comprising adhesive or binder to form a calcium-phosphate crystalline cement or paste.

6. The composition of claim 1 applied to the surfaces of solid materials for implantation.

7. The composition of claim 1 formed into ceramic blocks for implantation into gaps or areas of bone resorption.

8. The composition of claim 1 further comprising a biologically active molecule selected from the group consisting of bone morphogenic proteins, cytokines, antibiotics, chemotherapeutic agents, bone marrow or bone progenitor cells, and substances that diminish bone resorption.

9. The composition of claim 1 produced by forming clean bone particles into particles ranging in size of up to approximately 200 microns;

removing organic constituents with a combination of organic solvents, sonication, and plasma ashing at a temperature of less than 10° C. and in the absence of water.

10. The composition of claim 9 wherein organic constituents are removed to form a composition containing less than 2% of the total dry weight as organic material.

11. The composition of claim 10 wherein the remaining organic material is removed by reaction with an inorganic non-aqueous solvent under conditions equivalent to reaction with hydrazine at low temperatures overnight.

12. The composition of claim 10 wherein the remaining organic material is removed by plasma ashing at low temperature.

13. The composition of claim 1 wherein the bone is mature, mineralized bone.

14. The composition of claim 1 wherein the crystals are derived from a material selected from the group consisting of bone, dentin, enamel, cementum, and cartilage.

15. A method for treating a patient in need of treatment thereof with an effective amount of the composition of any one of claims 1 to 14.

16. The method of claim 14 wherein the composition is applied to replace bone lost due to disease or injury.

17. A method for making a prosthetic device comprising forming a substrate of the composition of any one of claims 1 to 14.

* * * * *